United States Patent [19]

Shturman

[11] Patent Number: 4,770,653
[45] Date of Patent: Sep. 13, 1988

[54] LASER ANGIOPLASTY

[75] Inventor: Leonid Shturman, Minnetonka, Minn.

[73] Assignee: Medilase, Inc., Minneapolis, Minn.

[21] Appl. No.: 66,937

[22] Filed: Jun. 25, 1987

[51] Int. Cl.$^4$ .............................................. A61N 1/30
[52] U.S. Cl. .................................... 604/21; 604/96; 128/6
[58] Field of Search ................... 604/20, 21, 95, 96; 128/4, 6, 657

[56] References Cited

U.S. PATENT DOCUMENTS

| Re. 32,421 | 5/1987 | Hattori . | |
|---|---|---|---|
| 3,448,739 | 6/1969 | Stark et al. . | |
| 3,470,876 | 10/1969 | Barchilon . | |
| 3,521,620 | 7/1970 | Cook . | |
| 3,547,103 | 12/1970 | Cook . | |
| 3,631,848 | 1/1972 | Muller . | |
| 4,040,413 | 8/1977 | Ohshiro . | |
| 4,054,128 | 10/1978 | Seufert et al. . | |
| 4,175,545 | 11/1979 | Termanini | 604/21 |
| 4,202,346 | 5/1980 | Granier . | |
| 4,277,168 | 7/1981 | Oku | 128/4 |
| 4,375,818 | 3/1983 | Suwaki et al. | 128/4 |
| 4,405,314 | 9/1983 | Cope . | |
| 4,418,688 | 12/1983 | Loeb . | |
| 4,419,987 | 12/1983 | Ogiu | 128/4 |
| 4,445,892 | 5/1984 | Hussein et al. | 128/4 |
| 4,448,188 | 5/1984 | Loeb . | |
| 4,517,974 | 5/1985 | Tanner . | |
| 4,519,390 | 5/1985 | Horne . | |
| 4,548,206 | 10/1985 | Osborne . | |
| 4,564,011 | 1/1986 | Goldman . | |
| 4,573,966 | 3/1986 | Weikl . | |
| 4,576,177 | 3/1986 | Webster . | |
| 4,627,436 | 12/1986 | Leckrone . | |
| 4,641,912 | 2/1987 | Goldenberg | 604/21 |
| 4,648,892 | 3/1987 | Kittrell . | |
| 4,654,024 | 3/1987 | Crittenden . | |
| 4,664,113 | 5/1987 | Frisbie et al. . | |
| 4,672,961 | 6/1987 | Davies . | |
| 4,674,497 | 6/1987 | Ogasawara . | |
| 4,681,104 | 7/1987 | Edelman . | |
| 4,699,463 | 10/1987 | D'Amelio et al. | 128/4 |

FOREIGN PATENT DOCUMENTS

| 85301123.7 | 9/1985 | European Pat. Off. . | |
|---|---|---|---|
| 86103432.0 | 9/1986 | European Pat. Off. . | |
| 82/01669 | 6/1983 | PCT Int'l Appl. . | |
| 84/02000 | 6/1985 | PCT Int'l Appl. . | |
| 86/01022 | 11/1986 | PCT Int'l Appl. . | |
| 1020124 | 5/1983 | U.S.S.R. | 128/4 |
| 2167668A | 6/1986 | United Kingdom . | |
| 2171913A | 9/1986 | United Kingdom . | |
| 2175505 | 12/1986 | United Kingdom . | |

OTHER PUBLICATIONS

*American Heart Journal*, 1986, vol. 3, pp. 1065-1072, article entitled "Steerable Fiberoptic Catheter Delivery of Laser Energy in Atherosclerotic Rabbits".
"History of Cardiac Catheterization", chapter 1, Herst M.D., pp. 1-9.
"Plaque Busters", *Forbes*, pp. 146-152, Jul. 28, 1986.
"Laser Angioplasty: State of the Art." Jeffrey Isner, M.D., *Tufts-New England Medical Center*, Boston, Mass.
"Coaxial Laser Energy Delivery Using a Steerable Catheter in Canine Coronary Arteries", *American Heart Journal*, vol. 113, No. 1, pp. 37-48, Jan. 1987.
"Excimers Lasers in Medicine" *Laser & Applications*, pp. 85-87, May 1986.

*Primary Examiner*—Stephen C. Pellegrino
*Assistant Examiner*—Ralph Lewis
*Attorney, Agent, or Firm*—Vidas & Arrett

[57] ABSTRACT

Aimable catheters for laser angioplasty, including at its distal end a positioning means carrying a laser radiation transmission means and/or optical viewing means, the positioning means being rotatable about an axis spaced from that of the catheter.

15 Claims, 2 Drawing Sheets

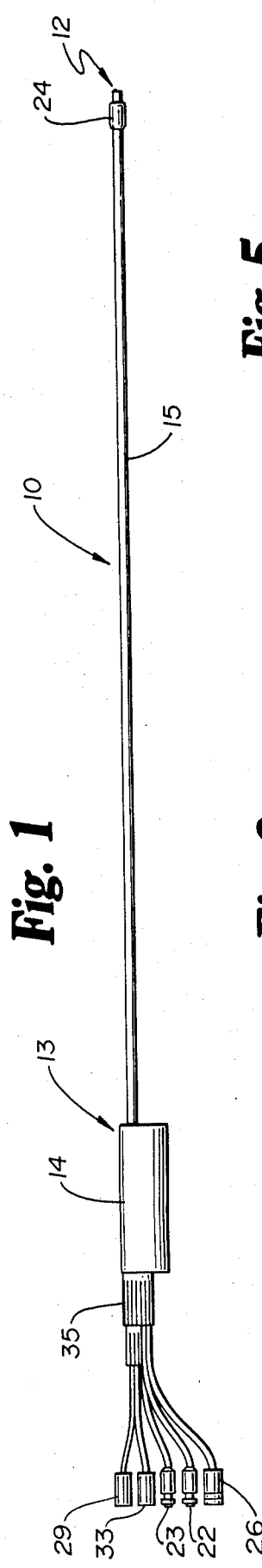
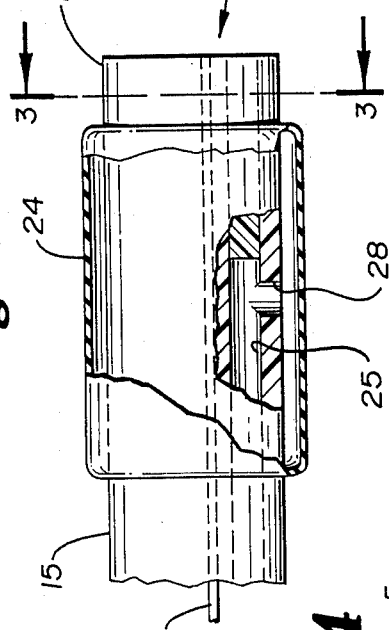
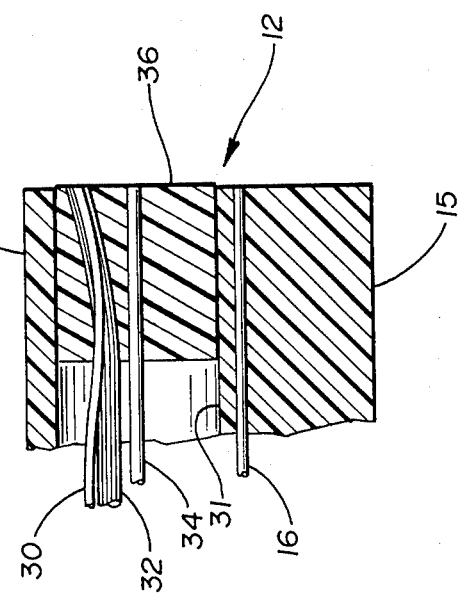
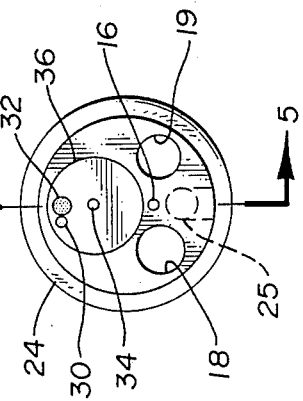

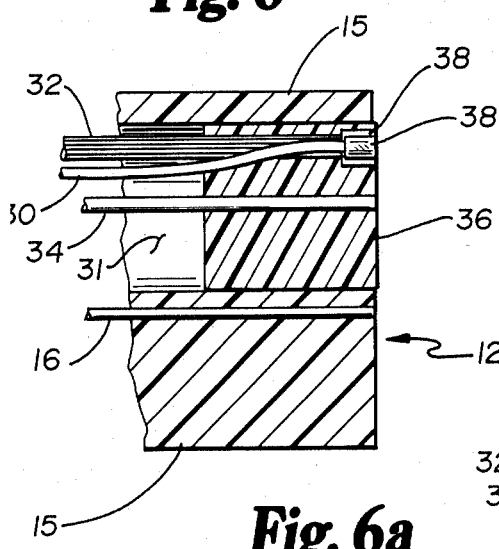
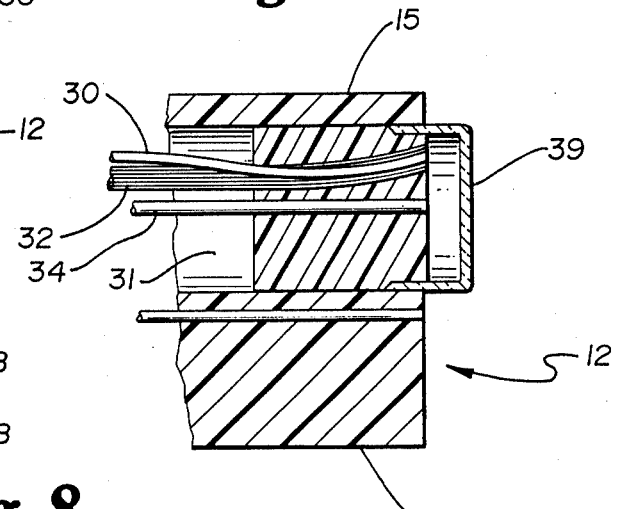
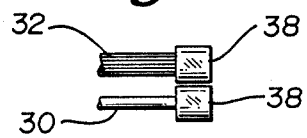
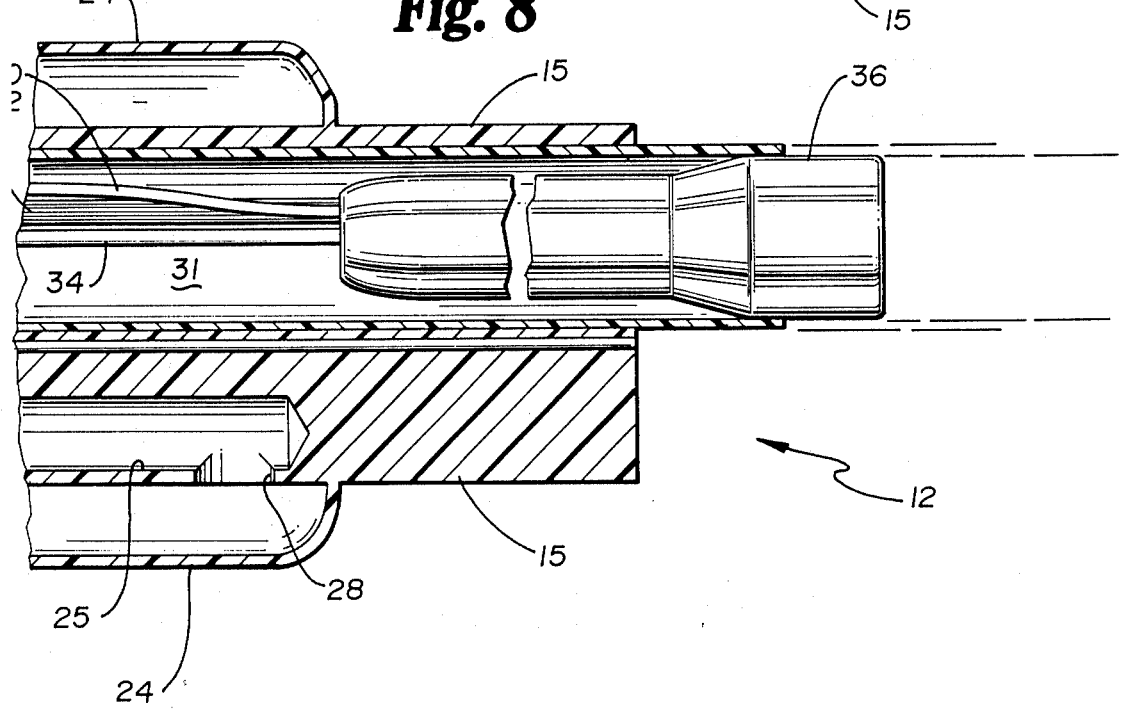

LASER ANGIOPLASTY

FIELD OF THE INVENTION

This invention relates to catheters and similar devices having a mechanism for aiming light transmitting fibers or other working means requiring remote control. Although particularly described with reference to laser angioplasty, the invention has broad applicability to various medical instruments such as endoscopes, angioscopes, catheters and microcatheters, and the like.

BACKGROUND OF THE INVENTION

This invention relates to medical instruments, in particular devices for performing laser surgery e.g., angioplasty, to treat atherosclerosis and the like. Atherosclerosis is a disease which causes the thickening and hardening of artery walls. It is characterized by lesions of raised atherosclerotic plaque which form within arterial lumens and occlude them partially or wholly. Coronary atherosclerosis is a leading cause of death in the United States. Atherosclerosis tends to increase progressively with age. The treatment of atherosclerosis typically consists of drug therapy, surgery or percutaneous angioplasty.

In percutaneous angioplasty, small balloon-tipped catheters were first developed which could be passed percutaneously into various arteries and then inflated to dilate areas of partial obstruction. While this procedure has gained a measure of acceptance as a less invasive alternative to surgery, balloon-angioplasty simply redistributes the atherosclerotic plaque. Frequency of recurrence or restenosis of the plaque occlusions has caused some concern about the efficacy of this technique.

Laser therapy has been suggested as another approach to percutaneous angioplasty. One technique utilizes laser technology to emit radiation onto a light receiving surface of a heat generating element. The light is converted by the element to heat. The element can then be contacted to material in a patient's body, such as a clot, atherosclerotic deposit or tissue, to alter same by melting, removing or destroying it.

In another laser technique, laser radiation is applied directly to the plaque deposit, clot or the like to vaporize or ablate it. It is this second technique to which the subject invention is most particularly directed. This particular technique of laser angioplasty provides the ability to remove the atherosclerotic plaque and reopen even totally occluded vessels without significant trauma to vessel wall with potentially reduced restenosis rate. However, the current technology for impinging laser radiation directly on a selected discrete treatment area has its own problems. Most critical has been the lack of ability to precisely aim laser radiation to the selected area to be treated without accidental arterial perforation.

In order to take full advantage of this approach to laser angioplasty, the present invention overcomes the aiming problem by providing fiber optic-based catheters which have at their distal ends a simple, fast and highly accurate aiming mechanism. The aiming mechanism allows the physician to precisely position an optic fiber, or any other positionable means or workpiece, at the distal end of a device by remote control. This gives the physician the ability to precisely aim at any point within the cross section of a vessel and direct the laser beam impingement upon plaque and the like from various angles with respect to the vessel wall.

The term "laser" is an acronym for Light Amplification by Stimulated Emission of Radiation. As used herein, the term is meant to encompass a device which utilizes the principle of amplification of electromagnetic waves by stimulated emission of radiation to produce coherent radiation in the infrared, visible or ultraviolet regions. Such radiation has already been used in medical applications.

Various types of lasers may be utilized in the context of the present invention. The pulsed energy source of the Excimer laser, having a coherent beam of ultraviolet radiation, is most preferred for cardiovascular use. The Excimer laser pinpoints and destroys tiny areas of plaque with short on-off energy bursts at the unusually low temperature of about 40° C., thereby avoiding such damage as burning surrounding tissue. The effect of the Excimer laser is believed to be one in which its radiation ruptures the molecular and chemical bonds of the plaque, rather than burning it, as do some other lasers. The plaque is ablated by using pulsed Excimer energy as brief as about 20 nanoseconds. It results in a clean smooth surface and is less likely than some other lasers to cause blood clots to form following the procedure. Although the subject invention may be utilized with a variety of different types of lasers, the Excimer laser is most preferred. Dye lasers and lasers on vapors of copper as well as other lasers may also be used.

Optical fibers and fiber bundles have also been used in a variety of medical applications. An optical fiber is a relatively flexible clad plastic or glass core wherein the cladding is of a lower index of refraction than the fiber core. When a plurality of such fibers are combined, a fiber optic bundle is produced. Optical fibers are flexible and are therefore capable of guiding light in a curved path defined by the placement of the fiber.

SUMMARY OF THE INVENTION

The aiming mechanism of the invention is applicable not only to laser angioplasty, but to angioscopes generally and to endoscopes as well as to other instruments and medical devices. However, it is particularly directed to catheters for laser angioplasty and is specifically described herein with reference to catheters for laser angioplasty.

In its most preferred form a device of the invention will comprise then a fiber optic catheter suitable for performing medical procedures in a vascular lumen or other cavity within a patient. The catheter will have a distal end to be inserted into a patient and a proximal end including a control handle held by a physician for directing the contemplated procedure. Such devices are typically constructed for disposal after a single use. More specifically, the catheter includes an elongated external tube containing a laser light transmitting means, such as an optical fiber. The catheter may also contain one or more fiber optic viewing bundles and may also be provided with one or more fluid passageways through which gases or liquids may be evacuated or transmitted. A guide wire may also be inserted through one of these conduits. Preferably, at least one expandable balloon is located near the distal end of the device. Expansion of the balloon increases the diameter of the distal end portion until it contacts the walls of the lumen to form a seal and also to stabilize the distal end of the catheter.

In accordance with the preferred embodiment of the invention, such instruments and devices include aiming means for positioning an optical fiber within an arterial lumen so as to direct the fiber toward a particular site therein. The aiming means comprises a rotatable positioning body carried at the distal end of the device. The positioning body is located in a displaced position with respect to the longitudinal axis (first axis) of the catheter device such that rotation of the catheter device about its longitudinal axis causes rotation of the positioning body about the longitudinal axis (first axis) of the cathether device. The optical fiber or other workpiece is received and held by the positioning body in a location displaced relative to the positioning body's axis of rotation (second axis) such that rotation of the positioning body rotates the optical fiber about the center of rotation of the positioning body. The combined rotational movements of the positioning body per se and the catheter device per se enables the physician to position and aim the optical fiber in any selected cross-sectional location in a vascular lumen or other cavity of a patient, as desired.

In one embodiment, the optical fiber or optical bundle is oriented slightly outwardly with respect to the longitudinal axis of the catheter device to orient and aim the fiber or bundle toward the wall of the lumen.

As already noted, in other embodiments of the invention, the positioning body may carry both an imaging fiber bundle and a lasing optical fiber or one or the other alone. Also, the positioning body may extend along and even beyond the entire length of the catheter device or may take the form of a relatively shortened body located only in the distal end portion of the device.

BRIEF DESCRIPTION OF THE DRAWINGS

FIG. 1 is an elevational view of a preferred embodiment of the medical device of the invention;

FIG. 2 is an enlarged detail view of the distal end of the device shown in FIG. 1, with parts broken away;

FIG. 3 is a sectional elevation taken along line 3—3 of FIG. 2;

FIG. 4 is a front elevational view of the distal end of the device of FIG. 2;

FIG. 5 is a sectional elevation taken along line 5—5 of FIG. 4 showing a modified preferred embodiment of the invention wherein the imaging and laser optical fiber conduits are positioned at a slight outward angle with respect to the longitudinal axis of the positioning means;

FIG. 6 is another preferred embodiment of the invention wherein the imaging and laser optical fibers are axis parallel with the respect to the longitudinal axis of the device and lenses are included at the distal ends of the imaging and laser optical fibers, respectively;

FIG. 6a is a schematic showing of the lens arrangement included in the embodiment of FIG. 6;

FIG. 7 is another embodiment showing a protective end cap on the device, and

FIG. 8 is another embodiment showing a telescoping version of the invention.

DESCRIPTION OF THE PREFERRED EMBODIMENT

While this invention can be embodied in many different forms, there are shown in the drawings and described in detail herein specific preferred embodiments of the invention. The present disclosure is an exemplification of the principles of the invention and is not intended to limit the invention to the particular embodiments illustrated.

The present invention in preferred form comprises a medical device for aiming any type of workpiece located at the end of a catheter-like instrument by remote control means. It is specifically described with reference to a medical device for delivering and applying laser radiation to a site in a vessel lumen of a patient. The radiation can be used to vaporize atherosclerotic plaque. Such instruments often times take the form of microcatheters of extremely small diameter. Such instruments are usually readily available in various diameter sizes to suit the particular work site in the lumen in which they are to be located. Thus a physician will have a number of various sized catheters at his disposal during any given procedure.

In some such devices, an elongated guide wire (not shown) may be selectively positioned within the lumen of the patient in association with the catheter. To this end, the catheter may include an elongated channel such as a slot, bore or conduit for slidably receiving the external guide wire situated along the catheter. The catheter can then be slid along the guide wire until a selected region of the patient's lumen has been reached. The aiming mechanism can be manipulated as desired and the laser radiation can then be selectively impinged on an area selected for treatment.

Some versions of such catheters are desirably constructed with at least a tip portion thereof including radio-opaque material (not shown). The radio-opaque material can then be used to locate the catheter under fluoroscopy.

Referring now particularly to FIGS. 1-3 of the drawing, a catheter device of the present invention in one embodiment comprises an elongated catheter, generally designated 10, having a working distal end generally designated 12. The device is adapted to be inserted into a patient and a remote control handle 14 is attached at a proximal control end 13 for manipulation and control by a physician. The catheter is flexible and generally comprises an extruded solid plastic body 15. Body 15 may consist of a single, soft, solid, extruded plastic material or it may consist of a plastic composite reinforced with plastic or metal braided filaments, such as Dacron ® polyester fiber or stainless steel. Typical plastics such as polytetrafluoroethylene, polyester, polyethylene and silicone may be used. A torque wire 16 extends through body 15 and is fixedly attached thereto, typically by extruding the catheter body around the torque wire. Torque wire 16 is attached at its proximal end to a knob 17 or the like so as to be rotatable therewith, whereby catheter body 15 may be rotated about its longitudinal axis during insertion and after reaching its desired location in a vessel lumen or the like.

When using the catheter in a vessel which contains an opaque fluid such as blood, it is often necessary to remove the opaque fluid and flush the area with a clear fluid such as saline solution to provide a viewable work area. To accomplish this, catheter body 15 may include conduits 18 and 19, which open at distal end 12 and which are respectively connected to tubes 20 and 21 at the proximal end. Conduits 18 and 19 may be formed during extrusion of body 15. Tubes 20 and 21 include appropriate fittings 22 and 23, which will be familiar to those of ordinary skill in the art. Conduits 18 and 19 may thus function as suction tubes, fluid flushing tubes, supply tubes or for receiving a guide wire, in the already known manner.

At the distal end 12 of catheter body 15, an expandable balloon 24 of the type already known in the art may also be included. In such an instance, another conduit 25 extends from connector 26 and tube 27 at the proximal end of the device to an opening 28 which communicate with expandable balloon 24 by means of which a fluid can be supplied to the balloon causing it to expand in the known manner. In this design version, when the balloon has been expanded, it will be necessary to contract it before rotating the catheter in situ.

Provision is made for delivering laser radiation to the distal end 12 of catheter 10 by providing a laser light source, (not shown). The laser may be coupled as is known in the art to control handle 14 through an optical coupling fitting 29. This arrangement in turn directs laser radiation through control handle 14 and through a laser radiation transmitting fiber 30 which may be located within an internal conduit 31 in body 15. Preferably, a single glass fiber 30 or other optical fiber with a core diameter of about 50 to about 600 microns is utilized for the laser radiation transmitting fiber 30. These are typical sizes presently available and are not critical; the smaller the better. It is most often desirable to use a single optical fiber for delivering of laser radiation. Such fibers are known in the art. However, other fiber arrangements may be used as they become available.

Additionally, a bundle of very flexible and very small diameter optical fibers 32 may be included and will also extend through conduit 31 from handle 14. Typically, such fibers are of plastic or glass and are known to the art. The proximal end thereof is appropriately connected to a fitting 33 to provide imaging or viewing in the known manner. Also conduit 31 includes a torque wire 34 which is connected and controlled at its proximal end by rotary knob 35.

With particular reference to FIG. 5, it can be seen that the distal ends of optical fiber 30, optical bundle 32 and torque wire 34 are received by rotatable positioning means, such as cylindrical body 36, which may be of plastic such as polypropylene, polytetrafluoroethylene or ultra high molecular weight polyethylene (UHMWPE). It may also be of metal such as stainless steel. Positioning means 36 is positioned or displaced off-axis relative to the longitudinal axis (first axis) of catheter body 15 (as best seen in FIGS. 3, 4 and 5) and is preferably of a diameter which is slightly larger than the radius of catheter body 15, as best seen in FIG. 3. As can be seen in FIGS. 3 and 5, optical fiber 30 and optical bundle 32 are located in positioning means 36 in a displaced position relative to its axis of rotation (second axis), which in this embodiment corresponds to the location of torque wire 34. Torque wire 34 is used for rotating the positioning means in catheter body 15. Positioning means 36 may be a relatively short body as shown in FIGS. 5-8, or it may be an elongated plastic body which extends throughout substantially the entire length of the catheter body 15 and conduit 31.

In the embodiment shown in FIGS. 4 and 5, it is to be noted that imaging bundle 32 and optical fiber 30 are positioned at a slight outward angle relative to the longitudinal axis of the catheter body 15. Such an outwardly directed positioning of the optical means allows a sweeping action of laser radiation and imaging to be directed toward the interior wall of the vascular lumen or cavity. However, as is seen in FIG. 6, the optical means 30 and 32 may also be positioned substantially parallel to the longitudinal axis of the catheter.

In use, the distal portion of the medical device is inserted into a patient and is positioned in the desired location. The balloon 24 is then inflated by means of the remote control handle 14 to occlude the blood vessel. A clear fluid such as saline or radio-opaque contrast material may be introduced through passageway conduit 18 or 19 allowing viewing through the imaging optical bundle 32. This allows visualizaton of the occlusion to be made prior to emission of laser radiation from the distal end of optical fiber 30. Such visualization also allows the physician to rotate catheter body 15, after contracting balloon 24, by rotation of torque wire 16 and knob 17 at remote control handle 14 and to also rotate the positioning body 36 by rotation of torque wire 34 and knob 35 at remote control handle 14 whereby optical fiber 30 and optical bundle 32 are aimed at the specific site upon which laser radiation is to be impinged. Readjustment of the position of the catheter and the positioning body at the operational site allows the laser radiation to be swept over all areas of an occlusion existing within the cross sectional area of the lumen.

As can be seen in the drawing (FIGS. 3, 4 and 5), positioning body 36 rotates about a second axis (its axis of rotation) which is displaced relative to the longitudinal or first axis of the catheter body 15 to provide for full coverage of the cross sectional area of the lumen in which the catheter is placed. This is also achieved by selecting the size of the diameter of body 36 relative to the radius of the catheter 15.

As already noted, a variety of working means other than optical fibers and optical bundles may be selectively positioned and aimed in this manner by the arrangement described above.

Referring now to FIGS. 6 and 6a, a modification is shown which includes lens arrangements 38 at the distal ends of fiber 30 and bundle 32, respectively. In the embodiments discussed previously (FIGS. 2-5) the field of view provided by imaging bundle 32 and the target area of fiber 30 were not necessarily exactly coincident. This may be achieved by orienting the fiber and bundle toward each other during fabrication. However, the embodiment of FIGS. 6 and 6a shows how this objective can be achieved by using optical lenses 38 to direct radiation or to otherwise focus it or control it. Such lenses may be of various known types and will preferably be, where possible, of the self-focusing type to allow attachment of the fiber and bundle directly to the lenses. In the case of the Excimer laser, it will probably be necessary to use quartz or synthetic fused silica lenses positioned with an air gap between them and the distal end of the optical fiber 30. Lenses will also protect the distal ends of the fiber and bundle.

Another embodiment of the invention is shown in FIG. 7. To protect the ends of optical fiber 30 and optical bundle 32, a radiation transparent end cap 39 of glass, quartz or the like may be included. It rotates with positioning body 36.

Yet another embodiment is shown in FIG. 8 wherein the positioning body 36 is not only rotatable but is constructed and arranged for translational movement in conduit 31 by pushing or pulling on control wire 34 via translational movement of knob 35.

As an alternate to extruding catheter body and the various conduits therein in a single piece, a series of different sized tubes may be combined to form the catheter. For example, a first tube may be used for body 15 and individual smaller tubes may be inserted into the first tube to form conduits 18, 19, 31, etc. Any empty space remaining within the first tube would be filled with plastic filler.

This completes the description of the preferred and alternate embodiments of the invention. Those skilled in the art may recognize other equivalents to the specific embodiment described herein which equivalents are intended to be encompassed by the claims attached hereto.

What is claimed is:

1. A medical device for insertion into remote locations and for being operated by remote control when so located, the device comprising:
a body adapted for insertion into a remote location and having a working distal end and having a proximal end control portion, the body, at least at the working distal end, being constructed and arranged for rotation about a longitudinal first axis;
positioning means carried at the working distal end of the body for rotation with the body about the first axis and for rotation with respect thereto about a second axis which is displaced relative to the longitudinal first axis, the second axis being located a fixed distance from the first axis and both axes extending out of the distal end;
means mounting the positioning means for rotation about the second axis;
working means carried by the positioning means in a location displaced relative to the second axis for rotation with the positioning means, said working means being oriented such that it faces out of the distal end of said body, and
remote control means at the proximal end portion operably connected to the positioning means for rotating it.

2. The device of claim 1 wherein the diameter of the positioning means associated with the second axis is larger than the radius of the body associated with the first axis.

3. A catheter comprising: an elongate catheter body adapted for insertion into a vessel and for rotation about a longitudinal first axis when in the vessel, the body having proximal and distal ends;
positioning means mounted at the distal end of the catheter body for rotation with the body about the first axis with respect thereto and about a second axis which is displaced relative to the first axis of the catheter body whereby the second axis is located a fixed distance from the first axis both axes extending out of the distal end;
working means carried by the positioning means for rotation therewith, the working means being carried thereby in a position displaced relative to the second axis and being oriented such that is faces out of the distal end of said body.

4. The catheter of claim 3 wherein the second axis is substantially parallel to the first axis.

5. The catheter of claim 3 including means operably connected to the positioning means for rotating it about the second axis.

6. A catheter comprising: an elongate catheter body adapted for insertion into a vessel and for rotation about a longitudinal first axis when in the vessel, the body having proximal and distal ends;
positioning means mounted at the distal end of the catheter body for rotation with the body about the first axis with respect thereto and about a second axis which is displaced relative to the first axis of the catheter body whereby the second axis is located a fixed distance from the first axis;
electromagnetic radiation transmission means carried by the positioning means for rotation therewith, the working means being carried thereby in a position displaced relative to the second axis.

7. A catheter comprising: an elongate catheter body adapted for insertion into a vessel and for rotation about a longitudinal first axis when in the vessel, the body having proximal and distal ends;
positioning means mounted at the distal end of the catheter body for rotation with the body about the first axis with respect thereto and about a second axis which is displaced relative to the first axis of the catheter body whereby the second axis is located a fixed distance from the first axis;
an optical fiber bundle where said bundle is operably connected to a receiving means at the proximal end, and carried by the positioning means for rotation therewith, the working means being carried thereby in a position displaced relative to the second axis.

8. A catheter comprising: an elongate catheter body adapted for insertion into a vessel and for rotation about a longitudinal first axis when in the vessel, the body having proximal and distal ends, and wherein the catheter body is of flexible plastic and includes a conduit at least at the distal end thereof;
positioning means comprising a body received by the conduit for rotation therein mounted at the distal end of the catheter body for rotation with the body about the first axis with respect thereto and about a second axis which is displaced relative to the first axis of the catheter body whereby the second axis is located a fixed distance from the first axis;
working means carried by the positioning means for rotation therewith, the working means being carried thereby in a position displaced relative to the second axis.

9. The catheter of claim 8 wherein the conduit extends substantially over the length of the catheter body as well as does the positioning means.

10. The catheter of claim 8 wherein the conduit is located in a displaced position with respect to the first axis.

11. A device for aiming high energy electromagnetic radiation from a laser source at an area within a blood vessel containing plaque, the device comprising:
a flexible elongate catheter body having proximal and distal end portions, the body being constructed and arranged for rotation about a first axis;
flexible elongate radiation transmitting means having proximate and distal ends and extending longitudinally through the catheter for transmitting radiation introduced at the proximal end to the distal end of the catheter, the distal end being constructed and arranged for directing transmitted radiation from the catheter;
positioning means mounted in the distal end portion of the catheter body for rotation with the body about the first axis and for rotation about a second axis which is displaced relative to the first axis of the catheter whereby the positioning means axis is located a fixed distance from the first axis, the positioning means including means for receiving and supporting the distal end of the radiation transmitting means in a displaced position relative to the second axis of rotation of the positioning means whereby rotation of the positioning means within the catheter controls the position of the end portion of the light transmitting means relative to the first axis of the catheter and rotation of at least the distal end portion of the catheter body when placed in a vessel and in combination with the foregoing rotation, controls the position of the end portion of the light transmitting means within the cross sectional area of the vessel to thereby allow aiming of the transmitted radiation within the vessel, and means operably connected to the positioning means for rotating it.

12. The catheter of claim 11 wherein the second axis is substantially parallel to the first axis.

13. The catheter of claim 11 wherein the catheter body includes a conduit at least in the distal end portion thereof, the conduit being displaced relative to the first axis of the catheter body, and the positioning means is received by the conduit for rotation therein.

14. The catheter of claim 13 wherein the catheter body is of a flexible plastic; the conduit extends over substantially its entire length and the positioning means is an elongate flexible body as well.

15. The catheter of claim 13 including a torque wire, one end of which is operably connected to the positioning means for controlling the rotation of the positioning means, the other end being attached to a rotation control means for controlling rotation of the torque wire.

* * * * *